United States Patent

Naumann et al.

[11] Patent Number: 5,728,886
[45] Date of Patent: Mar. 17, 1998

[54] COMPOUNDS OF THE PHOSPHINE GROUP, THEIR PREPARATION AND THEIR USE

[75] Inventors: Christoph Naumann, Niedernhausen; Dieter Regnat, Eppstein, both of Germany

[73] Assignee: Hoechst AG, Frankfurt, Germany

[21] Appl. No.: 510,789

[22] Filed: Aug. 3, 1995

[30] Foreign Application Priority Data

Aug. 5, 1994 [DE] Germany .................. 44 27 836.5

[51] Int. Cl.$^6$ .................................................. C07F 9/02
[52] U.S. Cl. .................................. 568/17; 568/12; 568/8
[58] Field of Search ........................... 568/8, 12, 17

[56] References Cited

U.S. PATENT DOCUMENTS 4,125,540  11/1978  Sugio et al. .................. 260/340
5,177,019   1/1993  Devon et al. ................. 436/104

FOREIGN PATENT DOCUMENTS 0 174 174  3/1986  European Pat. Off. .
0 503 884  9/1992  European Pat. Off. .

Primary Examiner—Marianne M. Cintins
Assistant Examiner—Dwayne C. Jones
Attorney, Agent, or Firm—Connolly & Hutz

[57] ABSTRACT

Phosphines of the formula (I) and the preparation of these phosphines

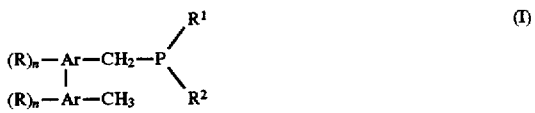

where Ar—Ar is a biphenyl radical, a 1-phenylnaphthyl radical or a 1,1'-binaphthyl radical, the $CH_2$ group and the $CH_3$ radical are each in the ortho position to the Ar—Ar bond, R is F, an alkyl radical or alkoxy radical each having from 1 to 8 carbon atoms, n is an integer from 0 to 4, $R^1$ and $R^2$ independently of one another, are an alkyl radical having from 1 to 10 carbon atoms, a cycloaliphatic radical having from 5 to 10 carbon atoms, or a radical $Ar^1$-$(R^3)_m$, where $Ar^1$ is a phenyl or naphthyl radical, $R^3$ is F, Cl, $CF_3$, $SO_3H$, $SO_3Me$ (Me=Li, Na or K), a dialkylamino radical having from 2 to 8 carbon atoms, an alkyl radical or alkoxy radical each having from 1 to 8 carbon atoms and m is an integer from 0 to 5, or $R^1$ and $R^2$ together with the phosphorus atom form a 4-membered to 8-membered ring to which can be fused.

35 Claims, No Drawings

COMPOUNDS OF THE PHOSPHINE GROUP, THEIR PREPARATION AND THEIR USE

Compounds of the phosphine group, processes for their preparation and their use

BACKGROUND OF THE INVENTION

1. Field of the Invention

The present invention relates to compounds of the phosphine group, processes for their preparation and their use.

2. Description of the Related Art

Phosphines have found many industrial applications. They are suitable, for example, as antioxidants, metal extractants, flameproofing agents, stabilizers for olefins (U.S. 6-400,168 (NTIS) abandoned on Mar. 1, 1988; Chem. Abstr. 100; 122286b) and trioxane (U.S. Pat. No. 4,125,540), starting compounds for Wittig reagents or ligands for metal complex catalysts.

Owing to their many forms, they also represent precursors for preparing further organic compounds which may or may not contain phosphorus.

SUMMARY OF THE INVENTION

Considering the wide-ranging importance attached to compounds of the phosphine group, it is a rewarding objective to provide new compounds from this group of substances, not only to supplement the range of their possible applications, but also to enrich and extend the range by subtle changes in material properties and variation of structural features.

This object is achieved by phosphines of the formula (I)

where Ar—Ar is a biphenyl radical, a 1-phenylnaphthyl radical or a 1,1'-binaphthyl radical, the $CH_2$ group and the $CH_3$ radical are each in the ortho position to the Ar—Ar bond, R is F, an alkyl radical or alkoxy radical each having from 1 to 8 carbon atoms, n is an integer from 0 to 4, $R^1$ and $R^2$ are identical or different and are each, independently of one another, an alkyl radical having from 1 to 10 carbon atoms, a cycloaliphatic radical having from 5 to 10 carbon atoms, or a radical $Ar^1$-$(R^3)_m$, where $Ar^1$ is a phenyl or naphthyl radical, $R^3$ is F, Cl, $CF_3$, $SO_3H$, $SO_3Me$ (Me=Li, Na or K), a dialkylamino radical having from 2 to 8 carbon atoms, an alkyl radical or alkoxy radical each having from 1 to 8 carbon atoms and m is an integer from 0 to 5, or $R^1$ and $R^2$ together with the phosphorus atom form a 4-membered to 8-membered ring to which can be fused, optionally, one or two aromatic rings or ring systems comprising from 6 to 10 carbon atoms.

DESCRIPTION OF THE PREFERRED EMBODIMENT

The preferred embodiment is related to a phosphine of the formula (I)

where Ar—Ar is a biphenyl radical, a 1-phenylnaphthyl radical or a 1,1'-dinaphthyl radical, the $CH_2$ group and the $CH_3$ radical are each in the ortho position to the Ar—Ar bond, R is F, an alkyl radical or alkoxy radical each having from 1 to 8 carbon atoms, n is an integer from 0 to 4, $R'$ and $R^2$ are identical or different and are each, independently of one another, an alkyl radical having from 1 to 10 carbon atoms, a cycloaliphatic radical having from 5 to 10 carbon atoms, or a radical $Ar^1$-$(R^3)_m$, where $Ar^1$ is a phenyl or naphthyl radical, $R^3$ is F, Cl, $CF_3$, $SO_3H$, $SO_3Me$ (Me=Li, Na or K), a dialkylamino radical having from 2 to 8 carbon atoms, an alkyl radical or alkoxy radical each having from 1 to 8 carbon atoms and m is an integer from 0 to 5, or $R^1$ and $R^2$ together with the phosphorus atom form a 4-membered to 8-membered ring to which can be fused, optionally one or two aromatic rings or ring system comprising from 6 to 10 carbon atoms. In addition, the invention is also related to a process to prepare the phosphines of formula (I).

Owing to their chemical behavior, which could be attributed to the incorporation of a trivalent phosphorus atom in the molecule, and because of their particular structure, the phosphines of the formula (I) represent interesting compounds. The particular structure of the phosphines is the result of the $H_3C$—$Ar(R)_n$—$Ar(R)_n$—$CH_2$ radical. A particular feature of the new phosphines is that many of these phosphines have one or more asymmetric centers. In a number of cases, the tertiary phosphorus atom can function as an asymmetric center. However, in many compounds there are also asymmetric centers resulting from the $H_3C$—$Ar(R)_n$—$Ar(R)_n$—$CH_2$ group.

The new phosphines of the formula (I) thus also open the door to the corresponding optically active isomers, for example to diastereomeric phosphines or to enantiomeric phosphines which in turn can be used, inter alia, as auxiliaries in carrying out asymmetric syntheses.

Furthermore, owing to their chemical behavior and their reactivity and because of their particular structure, the new phosphines can be used as building blocks for preparing further organic compounds which may or may not contain phosphorus.

Phosphines of the formula (I) in which Ar—Ar is a biphenyl radical, a 1-phenylnaphthyl radical or a 1,1'-binaphthyl radical and R is an alkyl radical or alkoxy radical each having from 1 to 4 carbon atoms play a particular role, since they are comparatively readily obtainable.

This also applies to phosphines of the formula (I) in which n is 0 or 1, in particular n is 0.

Of interest are also phosphines of the formula (I) in which $R^1$ and $R^2$ are identical or different and are each, independently of one another, an alkyl radical having from 1 to 6 carbon atoms, a cycloaliphatic radical having 5 or 6 carbon atoms or a radical $Ar^1$—$(R^3)_m$, where $Ar^1$ is a phenyl radical, $R^3$ is F, $CF_3$ or an alkyl radical having from 1 to 4 carbon atoms and m is 0 or 1, or $R^1$ and $R^2$ together with the phosphorus atom form a ring and are $CH_2$—$Ar(R)_n$—$Ar(R)_n$—$CH_2$.

If the phosphines of the formula (I) possess an asymmetric center and thus meet the conditions for the existence of optical isomers, they occur in the (R,S) form, in the (R) form or in the (S) form. Phosphines in the (R) form and the (S) form are of interest in connection with carrying out asymmetric syntheses.

They can be used with good prospects of success both in the (R) form or (S) form as optically active building blocks for synthesizing further compounds, which may or may not be optically active and may or may not contain phosphorus, in the (R) form or (S) form.

Of particular interest are phosphines of the formula (I) which are in the (R,S) form, in the (R) form or (S) form and in which Ar—Ar is 1,1'-binaphthyl and n may be 0 or 1, in particular 0. These compounds are not only readily available in the (R,S) form, but can also be prepared in either the (R) form or the (S) form with justifiable effort.

Without making any claims as to completeness, typical representatives of phosphines of the formula (I) which may be mentioned are the following compounds: (R,S)-2-diphenylphosphinomethyl-2'-methyl-1,1'-binaphthyl (R)-2-diphenylphosphinomethyl-2'-methyl-1,1'-binaphthyl (S)-2-diphenylphosphinomethyl-2'-methyl-1,1'-binaphthyl 2-diphenylphosphinomethyl-2'-methylbiphenyl (R,S)-2-diisopropylphosphinomethyl-2'-methyl-1,1'-binaphthyl (R)-2-diisopropylphosphinomethyl-2'-methyl-1,1'-binaphthyl (S)-2-diisopropylphosphinomethyl-2'-methyl-1,1'-binaphthyl (R,S)-2-dimethylphosphinomethyl-2'-methyl-1,1'-binaphthyl (R)-2-dimethylphosphinomethyl-2'-methyl-1,1'-binaphthyl (S)-2-dimethylphosphinomethyl-2'-methyl-1,1'-binaphthyl (R,S)-2-bis(1-methylpropyl)phosphinomethyl-2'-methyl-1,1'-binaphthyl (R)-2-bis(1-methylpropyl)phosphinomethyl-2'-methyl-1,1'-binaphthyl (S)-2-bis(1-methylpropyl)phosphinomethyl-2'-methyl-1,1'-binaphthyl (R,S)-2-bis(3-fluorophenyl)phosphinomethyl-2'-methyl-1,1'-binaphthyl (R)-2-bis(3-fluorophenyl)phosphinomethyl-2'-methyl-1,1'-binaphthyl (S)-2-bis(3-fluorophenyl)phosphinomethyl-2'-methyl-1,1'-binaphthyl (R,S)-2-bis(4-methoxyphenyl)phosphinomethyl-2'-methyl-1,1'-binaphthyl (R)-2-bis(4-methoxyphenyl)phosphinomethyl-2'-methyl-1,1'-binaphthyl (S)-2-bis(4-methoxyphenyl)phosphinomethyl-2'-methyl-1,1'-binaphthyl (R,S)-2-bis(4-N,N-dimethylaminophenyl)phosphinomethyl-2,-methyl-1,1'-binaphthyl (R)-2-bis(4-N,N-dimethylaminophenyl)phosphinomethyl-2'-methyl-1,1'-binaphthyl (S)-2-bis(4-N,N-dimethylaminophenyl)phosphinomethyl-2'-methyl-1,1'-binaphthyl (R,S)-6,6-dibromo-2-diphenylphosphinomethyl-2'-methyl-1,1'-binaphthyl (R)-6,6-dibromo-2-diphenylphosphinomethyl-2'-methyl-1,1'-binaphthyl (S)-6,6-dibromo-2-diphenylphosphinomethyl-2'-methyl-1,1'-binaphthyl (R,S)-2-bis(2-tolylphenyl)phosphinomethyl-2'-methyl-1,1'-binaphthyl (R)-2-bis(2-tolylphenyl)phosphinomethyl-2'-methyl-1,1'-binaphthyl (S)-2-bis(2-tolylphenyl)phosphinomethyl-2'-methyl-1,1'-binaphthyl The present invention further provides a process for preparing phosphines of the formula (I)

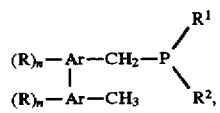

It comprises reacting a compound of the formula (II)

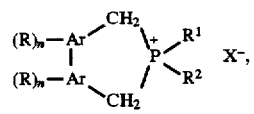

where Ar—Ar is a biphenyl radical, a 1-phenylnaphthyl radical or a 1,1'-binaphthyl radical, the $CH_2$ group is in each case in the ortho position to the Ar—Ar bond, R is F, an alkyl radical or alkoxy radical each having from 1 to 8 carbon atoms, n is an integer from 0 to 4, $R^1$ and $R^2$ are identical or different and are each, independently of one another, an alkyl radical having from 1 to 10 carbon atoms, a cycloaliphatic radical having from 5 to 10 carbon atoms, or a radical $Ar^1$-$(R^3)_m$, where $Ar^1$ is a phenyl or naphthyl radical, $R^3$ is F, Cl, $CF_3$, $SO_3H$, $SO_3Me$ (Me=Li, Na or K), a dialkylamino radical having from 2 to 8 carbon atoms, an alkyl radical or alkoxy radical each having from 1 to 8 carbon atoms and m is an integer from 0 to 5, or $R^1$ and $R^2$ together with the phosphorus atom form a 4-membered to 8-membered ring to which can be fused, optionally, one or two aromatic rings or ring systems comprising from 6 to 10 carbon atoms, and $X^-$ is a monovalent anion or the equivalent of a polyvalent anion of a mineral acid, carboxylic acid, sulfonic acid or of an alcohol, with an aqueous solution of a base, in the presence or absence of a solubilizer, isolating the phosphine oxide of the formula (III)

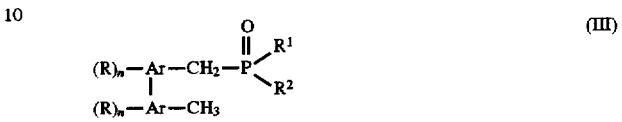

formed in the reaction and subsequently reducing the latter, in the presence or absence of an inert solvent, to give the phosphine of the formula (I), or reacting the compound of the formula (II), in the presence or absence of an inert solvent, directly with a reducing agent to give the phosphine of the formula (I).

The reaction proceeds either in two steps corresponding to the equations ($A_1$) and ($A_2$), where R, n, Ar—Ar, $R^1$ and $R^2$ in the phosphine oxide of the formula (III) formed in accordance with equation ($A_1$) have the same meaning as in formulae (I) and (II),

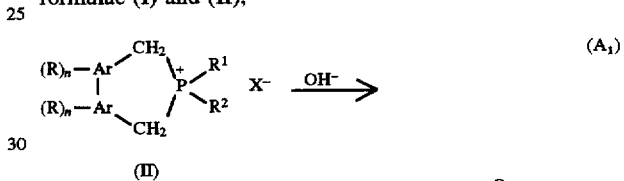

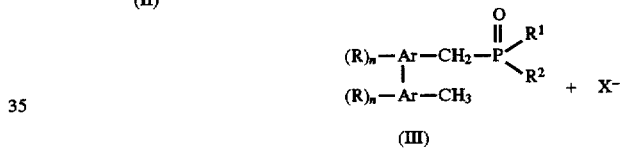

or it leads in accordance with equation (B)

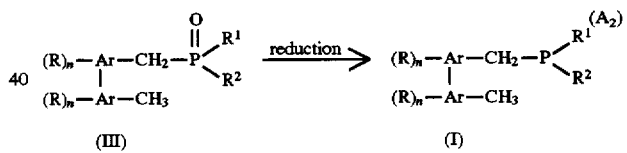

directly to the phosphine of the formula (I).

An advantage of the process of the invention is that comparatively readily available starting materials can be used. This applies both to the compounds of the formula (II) and to the auxiliaries (base and reducing agent). A further advantage is that the reaction can be carried out without great expense in terms of apparatus. Furthermore, the reaction proceeds with high selectivity and gives the desired end products (compounds of the formula (I)) in high yield. The purity of the end products thus formed is usually so good that a very pure end product can be obtained just by simple crystallization from the reaction mixture directly formed. An additional purification requiring further technical effort and generally resulting in a reduction in the yield can in this case be omitted.

For the process, a particular role is played by compounds of the formula (II) in which Ar—Ar is a biphenyl radical, a 1-phenylnaphthyl radical or a 1,1'-binaphthyl radical and R is an alkyl radical or alkoxy radical each having from 1 to 4 carbon atoms, since they are comparatively readily available and a very wide range thereof can be provided. This also applies to compounds of the formula (II) in which n is 0 or 1, in particular 0.

A further advantage of the process of the invention is that in a number of cases optically active phosphines of the formula (I) can be prepared either in the (R) form or in the (S) form.

It is generally known that it is very difficult to resolve a racemic mixture into enantiomerically pure or only substantially enantiomerically pure compounds. Such resolutions of racemates are generally very complicated and, in addition, are usually not successful.

By reaction of the compound of the formula (II) in the (R) form or in the (S) form in accordance with the equations ($A_1$) and ($A_2$) or (B), the process of the invention surprisingly provides a very simple route to the direct preparation of phosphines of the formula (I) in the (R) form and the (S) form. Since the (R) and the (S) forms of the phosphonium salts used as starting materials can be synthesized in a targeted manner and the reaction of the phosphonium salts (II) proceeding with ring opening and reduction does not lead to racemization or to a complete elimination of a phosphorus-containing organic compound, it is possible to omit a complicated resolution of a racemate, whose prospects of success are in any case very uncertain. The enantiomerically pure or substantially enantiomerically pure phosphonium salts can be obtained directly from the reaction mixture by simple crystallization and can be isolated by filtration.

Depending on what is required, a compound of the formula (II) in the (R,S) form, in the (R) form or in the (S) form is used to give the corresponding phosphine in the (R,S) form, in the (R) form or in the (S) form.

It is of particular interest to use compounds of the formula (II) in which Ar—Ar is 1,1-binaphthyl in the (R,S) form, in the (R) form and in the (S) form. In particular, it is interesting to use these compounds in the (R) form or the (S) form to prepare the corresponding phosphines.

Use is generally made of the compounds of the formula (II) in which $R^1$ and $R^2$ are identical or different and are each, independently of one another, an alkyl radical having from 1 to 6 carbon atoms, a cycloaliphatic radical having 5 or 6 carbon atoms or a radical $Ar^1$—$(R^3)_m$, where $Ar^1$ is a phenyl radical, $R^3$ is F, $CF_3$ or an alkyl radical having from 1 to 4 carbon atoms and m is 0 or 1, or $R^1$ and $R^2$ together with the phosphorus atom form a ring and are $CH_2$—Ar(R)$_n$—Ar(R)$_n$—$CH_2$.

As already mentioned above in connection with the compound of the formula (II), $X^-$ is a monovalent anion or the equivalent of a polyvalent anion of a mineral acid, carboxylic acid, sulfonic acid or an alcohol.

Without making any claims as to completeness, monovalent anions which may be mentioned are $F^-$, $Cl^-$, $Br^-$, $I^-$, $NO_3^-$, $HSO_4^-$, $HCO_3^-$, $BF_4^-$, $PF_6^-$, $H_2PO_4^-$, $ClO_4^-$, $R^4COO^-$, where $R^4$ is H, an alkyl radical having from 1 to 7 carbon atoms or an aryl radical having from 6 to 10 carbon atoms, $R^5SO_3^-$, where $R^5$ is an F, $CF_3$, $CH_3$, phenyl or tolyl radical, and $R^6O^-$, where $R^6$ is a radical having from 1 to 10 carbon atoms, and equivalents of a polyvalent anion which may be mentioned are ½ $SO_4^{2-}$, ½ $HPO_4^{2-}$, ½ $CO_3^{2-}$ or ½ anion of a dicarboxylic acid having from 2 to 6 carbon atoms.

The base usually used is an oxide, hydroxide or carbonate of an alkali metal or alkaline earth metal, in particular an alkali metal hydroxide or alkaline earth metal hydroxide.

The base is used in the form of an aqueous solution. The aqueous solution contains from 1 to 35, in particular from 2 to 30, preferably from 4 to 25, % by weight of base. Particularly suitable aqueous solutions are those containing NaOH, $Na_2CO_3$, KOH and/or $K_2CO_3$. The molar ratio of base to phosphonium salt is usually (2 to 60):1, in particular (6 to 40):1, preferably (10 to 30):1.

In a number of cases it can be useful to carry out the reaction of the compound of the formula (I) with the aqueous solution of the base in the presence of a solubilizer. However, it is also possible to omit the addition of a solubilizer, but in this case longer reaction times may have to be accepted.

Suitable solubilizers are polar, water-miscible solvents, for example aliphatic alcohols having from 1 to 4 carbon atoms, tetrahydrofuran, dioxane, acetonitrile, N,N-dimethylformamide or N,N-dimethylacetamide. It is also possible to use mixtures of these polar, water-miscible organic solvents as solubilizers. Other solubilizers which can be used are phase transfer catalysts, for example crown ethers such as 18-crown-6, or quaternary ammonium salts such as tetrabutylammonium salts.

If a polar, water-miscible organic solvent is used as solubilizer, the amount used is from 5 to 100, in particular from 10 to 50, % by volume, based on the volume of the aqueous solution of the base. If a phase transfer catalyst is to be used as solubilizer, an amount of from 0 to 5% by weight, based on the phosphonium compound of the formula (II), is usually found to be sufficient.

The reaction is usually carried out at from 0° to 120° C., in particular from 10° to 110° C., preferably from 20° to 100° C.

It is self-evident that good mixing has to be provided during the reaction.

The reaction of the phosphonium compound of the formula (II) with the base results in the formation in accordance with equation ($A_1$) of the phosphine oxide of the formula (III), which is isolated.

It is particularly simple to isolate the phosphine oxide of the formula (III) by extraction, for example by extraction using a water-insoluble organic solvent.

The extraction can be carried out by means of a chlorinated aliphatic hydrocarbon, an aromatic hydrocarbon, an aliphatic ketone having from 4 to 12 carbon atoms or an ester of an aliphatic carboxylic acid having from 2 to 6 carbon atoms, for example by means of methylene chloride, dichloroethane, chloroform, toluene, o-xylene, m-xylene, p-xylene, a mixture of isomeric xylenes, methyl acetate, ethyl acetate, 2-butanone or 3-pentanone.

Subsequently, the phosphine oxide of the formula (III), in the presence of absence of an inert solvent, is reduced by means of a hydride or by means of an organosilane, organodichlorosilane or trichlorosilane used in the presence or absence of a tertiary amine to give the phosphine of the formula (I). Suitable inert solvents are, for example, toluene, o-xylene, m-xylene, p-xylene, mixtures of isomeric xylenes, dioxane or acetonitrile or mixtures of these solvents.

Suitable hydrides are, for example, lithium aluminum hydride and suitable organodichlorosilanes are methyldichlorosilane, ethyldichlorosilane and phenyldichlorosilane.

The phosphine oxide of the formula (III) is usually reduced at from 20° to 170° C., in particular from 40° to 160° C., preferably from 60° to 150° C.

In a number of cases, the process of the invention can be structured particularly simply by not, as described above, forming the phosphine oxide of the formula (III) in accordance with equation (A₁) and subsequently reducing this in accordance with equation (A₂), but by converting the phosphonium compound of the formula (II) by reduction (reductive ring opening) directly into the phosphine of the formula (I) in accordance with equation (B). The reduction is carried out in the presence or absence of an inert solvent, for example tetrahydrofuran, dioxane, toluene, o-xylene, m-xylene, p-xylene, a mixture of isomeric xylenes, ethylbenzene, n-heptane or a high-boiling petroleum ether (boiling point ≧100° C.) using a hydride as reducing agent. Suitable hydrides are, for example, sodium hydride, potassium hydride, lithium aluminum hydride, sodium borohydride, diisobutylaluminum hydride or sodium dihydridobis(2-methoxy)aluminate, in particular sodium hydride, lithium aluminum hydride or sodium dihydridobis (2-methoxy) aluminate.

The compound of the formula (II) is reacted directly with the reducing agent at from 50° to 200° C., in particular from 60° to 160° C., preferably from 70° to 150° C., in accordance with equation (B) to give the phosphine of the formula (I).

The process of the invention can generally be carried out continuously or batchwise. It is particularly suitable for batchwise operation.

The phosphines of the formula (I) are suitable as antioxidants and as constituents of catalyst systems.

The following examples illustrate the invention without limiting it.

Experimental part

The Examples 1a to 4a relate to the preparation of phosphine oxides in accordance with equation (A₁), the Examples 1b to 4b relate to the reduction of the phosphine oxides in accordance with equation (A₂), while the Examples 5 to 9 demonstrate the direct reduction in accordance with equation (B).

EXAMPLE 1a

Preparation of 2-diphenylphosphinylmethyl-2'-methyl-1,1'-binaphthyl 4 g (7.3 mmol) of 4,4-diphenyl-4,5-dihydro-3H-dinaphtho-[2,1-c:1',2'-e]phosphepinium bromide are suspended in a mixture of 80 ml of 2N sodium hydroxide solution and 30 ml of ethanol and heated to boiling for 4 hours. The reaction solution is subsequently evaporated to dryness at 12 torr/40° C. The residue is taken up in 80 ml of dichloromethane and extracted twice with 30 ml of water each time. The organic phase is dried over sodium sulfate and evaporated to dryness at 12 torr/40° C. This gives colorless crystals (melting point: 199.5° C.).

Yield: 3.3 g (88% of theory)
$^{31}$P-NMR spectrum: (CDCl₃) δ=29.8 ppm
FAB mass spectrum: M⁺=483

EXAMPLE 1b

Preparation of 2-diphenylphosphinomethyl-2'-methyl-1,1'-binaphthyl by reduction of 2-diphenylphosphinylmethyl-2'-methyl-1,1'-binaphthyl with methyldichlorosilane 2.9 g (6.0 mmol) of 2-diphenylphosphinylmethyl-2'-methyl-1,1'-binaphthyl are suspended in 15 ml of xylene and 5.6 g (30 mmol) of tributylamine are added. The mixture is heated under reflux for 3 hours while stirring, to free the suspension of oxygen. It is subsequently cooled to room temperature and 3.3 g (29 mmol) of methyldichlorosilane are allowed to run in quickly from a dropping funnel. The mixture is heated under reflux, with the internal temperature slowly being increased from 100° C. to 146° C. over a period of from 12 to 13 hours. Xylene is subsequently distilled off under atmospheric pressure, the mixture is allowed to cool and the residue is admixed with i-propanol until crystallization occurs. The colorless crystals are filtered off with suction and dried at 12 torr/40° C.

Yield: 1.2 g (41.5% of theory)
Melting point: 134° C.
$^{31}$P-NMR spectrum: (Benzene-d₆) δ=–12.0 ppm

EXAMPLE 2a

Preparation of 2-di(1'-methylpropyl)phosphinylmethyl-2'-methyl-1,1'-binaphthyl 4 g (7.9 mmol) of 4,4-di(1'-methylpropyl)-4,5-dihydro-3H-dinaphthyl-[2,1-c:1',2'-e]phosphepinium bromide are reacted using a method analogous to Example 1a. This gives a colorless oil.

Yield: 3.3 g (99% of theory)
$^{31}$P-NMR spectrum (CDCl₃) 55.61 55.46 55.37 55.24 ppm in a ratio of 1:1:1:1
FAB mass spectrum M⁺=442

EXAMPLE 2b

Preparation of 2-di(1'-methylpropyl)phosphinomethyl-2'-methyl-1,1'-binaphthyl 2 g (4.52 mmol) of 2-di(1'-methylpropyl)phosphinylmethyl-2'-methyl-1,1'-binaphthyl are reacted using a method analogous to Example 1b.
This gives a colorless oil.

Yield: 1.24 g (65% of theory)
$^{31}$P-NMR spectrum (Benzene-d₆) δ=1.64; 0.70; 0.43; 0.04 ppm in a ratio of 1:1:1:1

EXAMPLE 3a

Preparation of 2-diisopropylphosphinylmethyl-2'-methyl-1,1'-binaphthyl 4 g (8.4 mmol) of 4,4-diisopropyl-4,5-dihydro-3H-dinaphtho-[2,1-c:1',2'-e]phosphepinium bromide are reacted using a method analogous to Example 1a. This gives a wax-like product.

Yield: 3.4 g (97% of theory)
$^{31}$P-NMR spectrum: (CDCl₃) δ=55.8 ppm
FAB mass spectrum: M⁺=414

EXAMPLE 3b

Preparation of 2-diisopropylphosphinomethyl-2'-methyl-1,1'-binaphthyl 2 g (4.83 mmol) of 2-diisopropylphosphinylmethyl-2'-methyl-1,1'-binaphthyl are reacted using a method analogous to Example 1b.
This gives a colorless oil.

Yield: 1.34 g (70% of theory)
$^{31}$P-NMR spectrum (Benzene-d₆) δ=7.70 ppm

EXAMPLE 4a

Preparation of 2-diphenylphosphinylmethyl-2'-methylbiphenyl 1.0 g (2.25 mmol) of 6,6-diphenyl-6,7-dihydro-5H-dibenzo-[c,e]phosphepinium bromide is reacted using a method analogous to Example 1.
This gives an oily product.

Yield: 600 mg (70% of theory)
$^{31}$P-NMR spectrum: (CDCl₃) δ=30.1 ppm

FAB mass spectrum: M$^{h+}$=382

EXAMPLE 4b

Preparation of 2-diphenylphosphinomethyl-2'-methylbiphenyl 2 g (5.23 mmol) of 2-diphenylphosphinylmethyl-2'-methylbiphenyl are reacted using a method analogous to Example 1b.
This gives colorless crystals (melting point (85°–86° C.).
Yield: 1.14 g (60% of theory)
$^{31}$P-NMR spectrum (Benzene-d$_6$) δ=–9.4 ppm

EXAMPLE 5

Preparation of 2-diphenylphosphinomethyl-2'-methyl-1,1'-binaphthyl 4 g (7.3 mmol) of 4,4-diphenyl-4,5-dihydro-3H-dinaphtho-[2,1-c:1',2'-e]phosphepinium bromide are suspended under a protective gas in 70 ml of absolute toluene. 500 mg (14.3 mmol) of lithium aluminum hydride are added to this suspension and the reaction solution is heated to boiling for 5 hours. Unreacted lithium aluminum hydride is subsequently filtered off. The organic phase is extracted with 20 ml of 1N sodium hydroxide solution and subsequently with 20 ml portions of water until the aqueous phase has a pH of from 6 to 7. The organic phase is dried over sodium sulfate and the toluene is drawn off at 12 torr/40° C. The wax-like residue is admixed with 15 ml of oxygen-free isopropanol, boiled and crystallized.
Yield: 2.4 g (71% of theory)
Melting point: 134° C.
$^{31}$P-NMR spectrum (Benzene-d$_6$) δ=–12.0 ppm
FAB mass spectrum: M$^{h+}$=466

EXAMPLE 6

Preparation of 2-diphenylphosphinomethyl-2'-methylbiphenyl 4 g (9.0 mmol) of 6,6-diphenyl-6,7-dihydro-5H-dibenzo-[c,e]phosphepinium bromide are suspended in 70 ml of absolute toluene under protective gas and reacted with 680 mg (18 mmol) of lithium aluminum hydride using a method analogous to Example 5.
This gives colorless crystals (melting point: 86° C).
Yield: 2.3 g (70 % of theory)
$^{31}$P-NMR spectrum (Benzene-d$_6$) δ=–9.3 ppm
FAB mass spectrum: M$^{h+}$=366

EXAMPLE 7

Preparation of 2-di(1'-methylpropyl)phosphinomethyl-2'-methyl-1,1'-binaphthyl 4 g (7.9 mmol) of 4,4-di(1'-methylpropyl)-4,5-dihydro-3H-dinaphtho[2,1-c:1',2'-e]phosphepinium bromide are suspended in 70 ml of absolute xylene and reacted with 400 mg (10.5 mmol) of lithium aluminum hydride using a method analogous to Example 5.
This gives a colorless oil.
Yield: 3.0 g (88% of theory)
$^{31}$P-NMR spectrum: (Benzene-d$_6$) δ=1.64; 0.70; 0.43; 0.04 ppm in a ratio of 1:1:1:1
FAB mass spectrum: M$^{h+}$=426

EXAMPLE 8

Preparation of 2-diisopropylphosphinomethyl-2'-methyl-1,1'-binaphthyl 4 g (8.4 mmol) of 4,4-diisopropyl-4,5-dihydro-3H-dinaphtho[2,1-c:1',2'-e]phosphepinium bromide are suspended in 70 ml of absolute toluene under protective gas and reacted with 400 mg (10.5 mmol) of lithium aluminum hydride using a method analogous to Example 5.
This gives a colorless oil.
Yield: 2.9 g (88 % of theory);
$^{31}$P-NMR spectrum (Benzene-d$_6$) δ=7.69 ppm
FAB mass spectrum: M$^{h+}$=398

EXAMPLE 9

Preparation of (S)-2-diphenylphosphinomethyl-2'-methyl-1,1'-binaphthyl 1 g (1.83 mmol) of (S)-4,4-diphenyl-4,5-dihydro-3H-dinaphtho[2,1-c:1',2'-e]phosphepinium bromide is suspended in 40 ml of absolute toluene under protective gas and reacted with 200 mg (5.7 mmol) of lithium aluminum hydride using a method analogous to Example 5.
Yield: 500 mg (58.9% of theory) [α]$^{20}_D$=–138.4° (measured in dichloromethane)
Melting point: from 131° to 132° C.
$^{31}$P-NMR spectrum (Benzene-d$_6$) δ=–11.86 ppm
FAB mass spectrum: M$^{h+}$=466

We claim:

1. A phosphine of the formula (I)

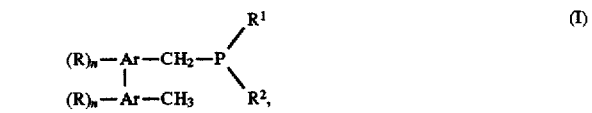

where Ar—Ar is a biphenyl radical, a 1-phenylnaphthyl radical or a 1,1'-binaphthyl radical, the CH$_2$ group and the CH$_3$ radical are each in the ortho position to the Ar—Ar bond, R is F, an alkyl radical or alkoxy radical each having from 1 to 8 carbon atoms, n is an integer from 0 to 4, R$^1$ and R$^2$ are identical or different and are each, independently of one another, an alkyl radical having from 1 to 10 carbon atoms, a cycloaliphatic radical having from 5 to 10 carbon atoms, or a radical Ar$^1$–(R$^3$)$_m$, where Ar$^1$ is a phenyl or naphthyl radical, R$^3$ is F, Cl, CF$_3$, SO$_3$H, SO$_3$Me (Me=Li, Na or K), a dialkylamino radical having from 2 to 8 carbon atoms, an alkyl radical or alkoxy radical each having from 1 to 8 carbon atoms and m is an integer from 0 to 5, or R$^1$ and R$^2$ together with the phosphorus atom form a 4-membered to 8-membered ring to which can be fused, if desired, one or two aromatic rings or ring systems comprising from 6 to 10 carbon atoms.

2. A phosphine as claimed in claim 1, wherein Ar—Ar is a biphenyl radical, a 1-phenylnaphthyl radical or a 1,1'-binaphthyl radical and R is an alkyl radical or alkoxy radical each having from 1 to 4 carbon atoms.

3. A phosphine as claimed in claim 1, wherein n is 0 or 1.

4. A phosphine as claimed in claim 1,
   wherein n is 0.

5. A phosphine as claimed in claim 1,
   wherein R$^1$ and R$^2$ are identical or different and are each, independently of one another, an alkyl radical having from 1 to 6 carbon atoms, a cycloaliphatic radical having 5 or 6 carbon atoms or a radical Ar$^1$—(R$^3$)$_m$, where Ar$^1$ is a phenyl radical R$^3$ is F, CF$_3$ or an alkyl radical having from 1 to 4 carbon atoms and m is 0 or 1, or R$^1$ and R$^2$ together with the phosphorus atom form a ring and are CH$_2$—Ar(R)$_n$—Ar(R)$_n$—CH$_2$.

6. A phosphine as claimed in claim 1, which is in the (R,S) form, (S,R) form, (R,R) form or (S,S) form.

7. A phosphine as claimed in claim 1, which is in the (R,S) form, (S,R) form, (R,R) form or (S,S) form and in which Ar—Ar is 1,1'dinaphthyl.

8. A process for preparing phosphines of the formula (I)

which comprises reacting a compound of the formula (II)

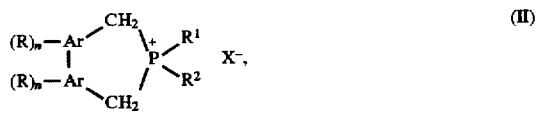

where Ar—Ar is a biphenyl radical, a 1-phenylnaphthyl radical or a 1,1'-binaphthyl radical, the $CH_2$ group is in each case in the ortho position to the Ar—Ar bond, R is F, an alkyl radical or alkoxy radical each having from 1 to 8 carbon atoms, n is an integer from 0 to 4, $R^1$ and $R^2$ are identical or different and are each, independently of one another, an alkyl radical having from 1 to 10 carbon atoms, a cycloaliphatic radical having from 5 to 10 carbon atoms, or a radical $Ar^1$–$(R^3)_m$, where $Ar^1$ is a phenyl or naphthyl radical, $R^3$ is F, Cl, $CF_3$, $SO_3H$, $SO_3Me$ (Me=Li, Na or K), a dialkylamino radical having from 2 to 8 carbon atoms, an alkyl radical or alkoxy radical each having from 1 to 8 carbon atoms and m is an integer from 0 to 5, or $R^1$ and $R^2$ together with the phosphorus atom form a 4-membered to 8-membered ring to which can be fused, if desired, one or two aromatic rings or ring systems comprising from 6 to 10 carbon atoms, and $X^-$ is a monovalent anion or the equivalent of a polyvalent anion of a mineral acid, carboxylic acid, sulfonic acid or of an alcohol, with an aqueous solution of a base, in the presence or absence of a solubilizer, isolating the phosphine oxide of the formula (III)

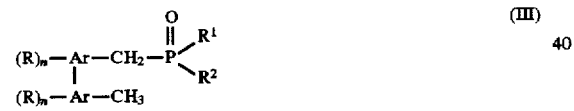

formed in the reaction and subsequently reducing the latter, in the presence or absence of an inert solvent, to give the phosphine of the formula (I), or reacting the compound of the formula (II), in the presence or absence of an inert solvent, directly with a reducing agent to give the phosphine of the formula (I).

9. The process as claimed in claim 8, wherein the compound of the formula (II) used is one in which Ar—Ar is a biphenyl radical, a 1-phenylnaphthyl radical or a 1,1'-binaphthyl radical and R is an alkyl radical or alkoxy radical each having from 1 to 4 carbon atoms.

10. The process as claimed in claim 8, wherein the compound of the formula (II) used is one in which n is 0 or 1.

11. The process as claimed in claim 8, wherein the compound of the formula (II) used is one in which n is 0.

12. The process as claimed in claim 8, wherein the compound of the formula (II) used is in the (R,S) form, (S,R) form, (R,R) form or (S,S) form.

13. The process as claimed in claim 8, wherein the compound of the formula (II) used is in the (R,S) form, (S,R) form, (R,R) form or (S,S) form and is a compound in which Ar—Ar is 1,1'binaphthyl.

14. The process as claimed in claim 8, wherein the compound of the formula (II) used is one in which $R^1$ and $R^2$ are identical or different and are each, independently of one another, an alkyl radical having from 1 to 6 carbon atoms, a cycloaliphatic radical having 5 or 6 carbon atoms or a radical $Ar^1$—$(R^3)_m$, where $Ar^1$ is a phenyl radical, $R^3$ is F, $CF_3$ or an alkyl radical having from 1 to 4 carbon atoms and m is 0 or 1, or $R^1$ and $R^2$ together with the phosphorus atom form a ring and are $CH_2$—$Ar(R)_n$—$Ar(R)_n$—$CH_2$.

15. The process as claimed in claim 8, wherein the base used is an oxide, hydroxide or carbonate of an alkali metal or an alkaline earth metal.

16. The process as claimed in claim 8, wherein a polar, water-soluble organic solvent or a phase transfer catalyst is used as solubilizer.

17. The process as claimed in claim 8, wherein an aliphatic alcohol having from 1 to 4 carbon atoms, tetrahydrofuran, dioxane, acetonitrile, N,N-dimethylformamide or N,N-dimethylacetamide is used as solubilizer.

18. The process as claimed in claim 8, wherein the compound of the formula (II) is reacted with the aqueous solution of the base at from 0° to 120° C.

19. The process as claimed in claim 8, wherein the phosphine oxide of the formula (III) is isolated by extraction using a water-insoluble organic solvent.

20. The process as claimed in claim 8, wherein the phosphine oxide of the formula (III) is reduced in the presence of toluene, o-xylene, m-xylene, p-xylene, mixtures of isomeric xylenes, dioxane or acetonitrile as inert solvent.

21. The process as claimed in claim 8, wherein the phosphine oxide of the formula (III) is reduced by means of a hydride or by means of an organosilane, organodichlorosilane or trichlorosilane used in the presence or absence of a tertiary amine.

22. The process as claimed in claim 8, wherein the phosphine oxide of the formula (III) is reduced with lithium aluminum hydride.

23. The process as claimed in claim 8, wherein the phosphine oxide of the formula (III) is reduced with methyldichlorosilane, ethyldichlorosilane or phenyldichlorosilane.

24. The process as claimed in claim 8, wherein the phosphine oxide of the formula (III) is reduced at from 20° to 170° C.

25. The process as claimed in claim 8, wherein the compound of the formula (II) is reacted with a reducing agent in the presence of tetrahydrofuran, dioxane, toluene, o-xylene, m-xylene, p-xylene, a mixture of isomeric xylenes, ethylbenzene as inert solvent to give the phosphine of the formula (I).

26. The process as claimed in claim 8, wherein the compound of the formula (II) is reacted with a hydride as reducing agent to give the phosphine of the formula (I).

27. The process as claimed in claim 8, wherein the compound of the formula (II) is reacted with sodium hydride, potassium hydride, lithium aluminum hydride, sodium borohydride, diisobutylaluminum hydride, sodium dihydridobis(2-methoxyethoxy) aluminate to give the phosphine of the formula (I).

28. The process as claimed in claim 8, wherein the compound of the formula (II) is reacted with the reducing agent at from 50° to 200° C. to give the phosphine of the formula (I).

29. The process as claimed in claim 8, wherein the compound of the formula (II) is reacted with the aqueous solution of the base at from 20° to 100° C. and the phosphine oxide of the formula (III) is reduced at from 40° to 160° C.

30. The process as claimed in claim 8, wherein the phosphine oxide of the formula (III) is reduced at from 60° to 150° C.

31. The process as claimed in claim 8, wherein the compound of the formula (II) is reacted with the reducing agent at from 60° to 160° C. to give the phosphine of the formula (I).

32. The process as claimed in claim 8, wherein the compound of the formula (II) is reacted with the reducing agent at from 70° to 150° C. to give the phosphine of the formula (I).

33. The process as claimed in claim 8, wherein Ar—Ar is a 1-phenylnaphthyl radical or a 1,1'-dinaphthyl radical.

34. The process as claimed in claim 18, wherein the compound of the formula (II) is reacted with the aqueous solution of the base at from 10° to 110° C.

35. A method of using the phosphine compound of claim 1 as an anti-oxidant.

* * * * *